United States Patent
Peterson

(10) Patent No.: US 8,182,585 B2
(45) Date of Patent: May 22, 2012

(54) SYSTEM AND METHOD OF CONTROLLING DUST AND/OR ODORS WITH A BLOWER UNIT AND A DEPLOYABLE BAFFLE MEMBER

(75) Inventor: Edwin Peterson, Brimfield, IL (US)

(73) Assignee: Dust Control Technology, Inc., Peoria, IL (US)

( * ) Notice: Subject to any disclaimer, the term of this patent is extended or adjusted under 35 U.S.C. 154(b) by 675 days.

(21) Appl. No.: 12/276,605

(22) Filed: Nov. 24, 2008

(65) Prior Publication Data

US 2010/0126340 A1 May 27, 2010

(51) Int. Cl.
*B01D 47/06* (2006.01)

(52) U.S. Cl. ............ 95/216; 96/277; 96/324; 96/325; 96/360

(58) Field of Classification Search ............ 95/216–218, 95/224, 270, 273, 32; 96/281–282, 322–328, 96/360, 366, 370, 256; 422/4, 124
See application file for complete search history.

(56) References Cited

U.S. PATENT DOCUMENTS

| | | | |
|---|---|---|---|
| 3,582,051 A | | 6/1971 | Klein |
| 4,156,436 A | | 5/1979 | Hawk |
| 5,211,336 A | * | 5/1993 | Kaidonis et al. ............ 239/1 |
| 5,816,537 A | * | 10/1998 | Pascoe et al. ............ 244/153 R |
| 6,223,995 B1 | | 5/2001 | Evans |
| 6,336,594 B1 | * | 1/2002 | Bader et al. ............ 239/54 |
| 7,036,798 B1 | | 5/2006 | Olson |
| 2003/0062174 A1 | * | 4/2003 | Passoni et al. ............ 169/46 |
| 2004/0195435 A1 | * | 10/2004 | Logosz ............ 244/15 |
| 2005/0046197 A1 | * | 3/2005 | Kingsley ............ 290/55 |
| 2007/0186778 A1 | * | 8/2007 | Peterson ............ 96/281 |
| 2009/0166444 A1 | * | 7/2009 | Peterson ............ 239/13 |

FOREIGN PATENT DOCUMENTS

| | | | |
|---|---|---|---|
| JP | EP0924475 A1 | * | 6/1999 |
| JP | EP924475 A1 | * | 6/1999 |

OTHER PUBLICATIONS

Ricker, Thomas, Airbeams: U.S. Army inflatable structures, www.engadget.com, Jun. 18, 2005, 7 pages, obtained from http://www.engadget.com/2005/06/08/airbeams-u-s-army-inflatable-structures/.
Tension Fabric Structures, Pink Inc. Photo Gallery, http://www.pinkinc.org/gallery/album02/Pink_Arch_05, 1 page photograph, date unknown, admitted prior art.
Inflate—Design and Manufacture of Inflatable Structures and Architecture, obtained from http://www.inflate.co.uk/i-structures.html, 1 page, date unknown, admitted prior art.
Kites: General Kite Info and a bit of tech, Kitemare.com, obtained from http://www.kitemare.com/Kitesurfing%20Kites.htm, 8 pages, date unknown, admitted prior art.

* cited by examiner

*Primary Examiner* — Duane Smith
*Assistant Examiner* — Ives Wu
(74) *Attorney, Agent, or Firm* — Barnes & Thornburg LLP

(57) ABSTRACT

A system and method for controlling dust and/or odors comprises a blower unit and baffle member deployed downstream of the blower unit. The blower unit comprises a fan propelled mister with a discharge tube and a fan disposed in the discharge tube adapted for drawing air into the discharge tube and creating a high velocity air flow exiting therefrom. The discharge tube has a plurality of nozzles and a fluid source is placed in communication with the nozzles such that the nozzles discharge fluid particles that are entrained in a high velocity air flow exiting from the discharge tube distal end. A baffle member is deployed downstream of the blower unit at an elevation above the blower unit so as to alter a flow path of ambient air flowing through a discharge path of the blower unit.

21 Claims, 7 Drawing Sheets

SYSTEM AND METHOD OF CONTROLLING DUST AND/OR ODORS WITH A BLOWER UNIT AND A DEPLOYABLE BAFFLE MEMBER

BACKGROUND

The disclosure herein relates in general to systems and methods for suppressing dust and/or odors by using a blower unit and a baffle member deployed downstream of the blower unit that creates ambient air conditions in the discharge path of blower unit conducive for the mist discharged from the blower unit to capture dust and/or odors particles in the ambient air and settle and entrap the captured particles on the ground.

Figure 1:
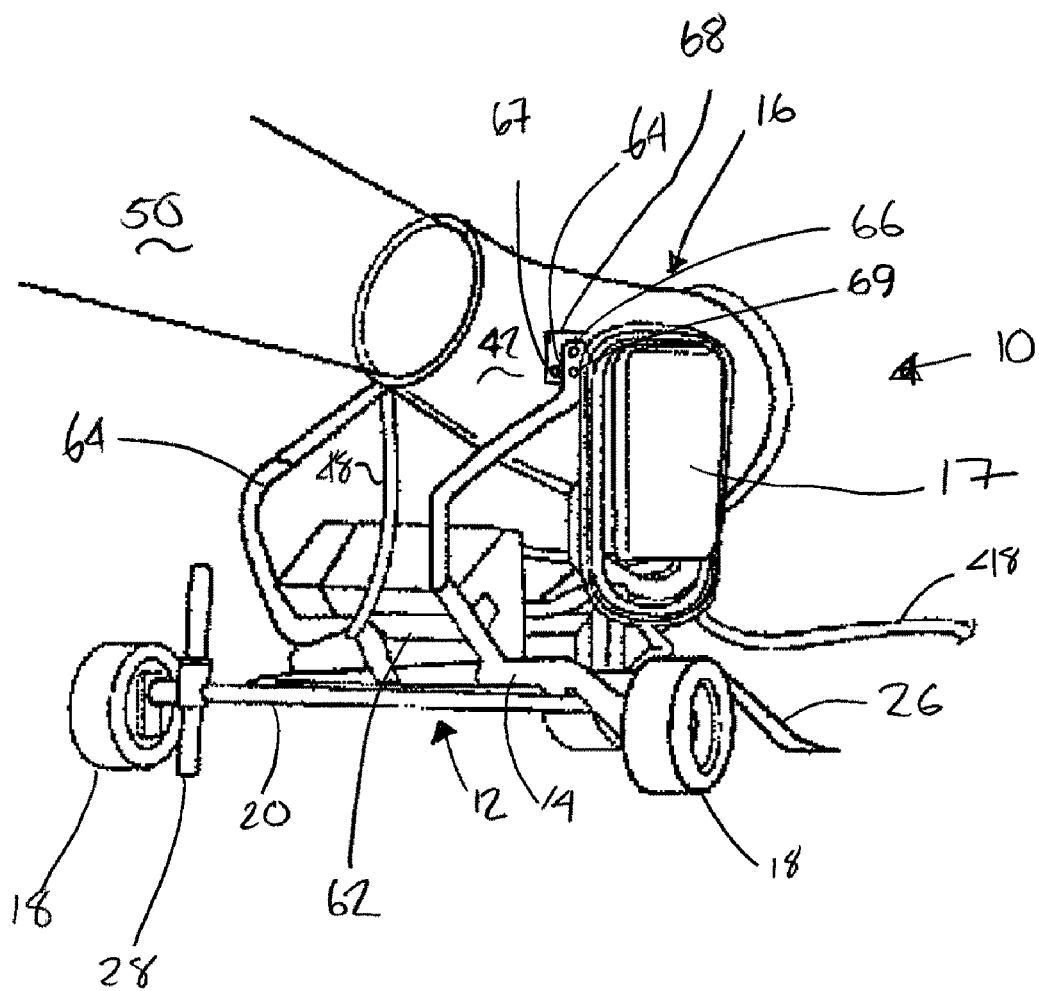
FIG. 1 is a perspective view of one embodiment of a blower unit in operation in accordance with the principles of the disclosure;

FIG. 2 is a rear elevation view of the blower unit shown in FIG. 1 with a portion of a grate of a fan propelled mister of the blower unit cut-away to show internal components of the fan propelled mister;

FIG. 3 is a partial perspective view of the blower unit of FIG. 1 showing a plurality of nozzles on a discharge end of the blower unit creating a mist;

FIG. 4 shows the blower unit of FIG. 1 in operation with one embodiment of a baffle member deployed downstream of the blower unit to alter the ambient air flow and create ambient air conditions in the discharge path of the blower unit conducive for the mist discharged from the blower unit to capture dust and/or odor particles contained in ambient air;

FIG. 5 shows the blower unit of FIG. 1 in operation with an alternate embodiment of the baffle member of FIG. 4 deployed downstream;

FIG. 6 shows the blower unit of FIG. 1 in operation with another alternate embodiment of the baffle member of FIG. 4 deployed downstream;

FIG. 7 shows the blower unit of FIG. 1 in operation with another alternate embodiment of the baffle member of FIG. 4 deployed downstream; and FIG. 8 shows a cross-sectional view of an embodiment of a baffle member, such as the baffle member shown in FIG. 6 or 7, with louvers and a dust collection apparatus disposed in an interior of the baffle member.

DETAILED DESCRIPTION OF THE DISCLOSED EMBODIMENTS

Referring now to the drawings, and particularly to FIGS. 1-3, there is shown a blower unit generally indicated by reference character 10. Several uses and configurations of blower units are disclosed in commonly assigned patent applications currently pending, including U.S. application Ser. Nos. 11/383,293 and 11/966,568, the disclosures of which are incorporated herein by reference. The blower unit as disclosed and claimed herein may have a configuration as disclosed in these applications or otherwise, for instance, the configuration described in greater detail below. The blower unit 10 may have a base 12 and a frame 14 for supporting a fan propelled mister 16. The blower unit may also comprise a control panel 17 to allow for the localized operation and control of the device, and the frame may support auxiliary equipment associated with the blower unit such as a compressor and a dosing pump (both not shown). The base preferably includes a plurality of wheels 18 that are rotatably connected to the base through an axle 20 located at or proximate to the front end of the base and an arm 22 located at or proximate to the rear of the base. While the base is shown as being generally triangular in shape, a variety of shapes may also be used. For instance, the base may comprise any type of structure to or on which the blower unit is attached, including but not limited to, a crane, a platform, a skid steer, or a post. In order to assist in moving the blower unit, a tow or push bar 26 may extend from the base, or a coupler member may extend outward from the base for attaching to a corresponding coupling member on a tow vehicle (not shown). The tow or push bar may also be designed to contact the ground to provide additional support for the device during operation. Additionally, the device may include posts 28 having platforms 30 that are movably attached to the base to permit the platforms to be slid in and out of contact with the ground to inhibit or facilitate movement of the device, respectively.

Referring to FIG. 2, the blower unit fan propelled mister 16 includes a fan 32 having a hub 34 and a plurality of blades 36 within a housing 38. A grate or mesh 40 preferably covers the back of the housing and the fan to permit air but not large foreign objects to be drawn into the fan during use. The housing of the fan propelled mister 16 preferably includes a discharge tube 42 to permit the generation of the high velocity air flow from the fan through the fan propelled mister. A fan motor (not shown) may be mounted in the housing, the hub or elsewhere for rotating the plurality of blades. Power may be supplied to the fan motor in any number of ways, including, but not limited to: through batteries, connecting an electrical cord to an electrical outlet or other power source, or through an engine. A switch (not shown) electrically connected to the fan motor to permit the fan propelled mister to be selectively operated may be located on the control panel 17.

As shown best in FIG. 3, a misting ring 44 having a plurality of nozzles 46 is preferably attached or connected to the end of the discharge tube 42. The nozzles 46 may be used to generate different sized fluid (e.g., water) particles. Nozzles providing different sized fluid particles may be alternated, or otherwise located about a single ring, or concentric rings each having different size nozzles. The nozzles may be made of brass, stainless steel or nylon, and may be sized as necessary for a particular application. For instance, in order to control dust, the nozzles may generate water or mist particles wherein the water particles fall within the range of 50 to 200 microns. The nozzles may also be sized to control odor. It has been found that forming water or mist particles that fall within the range of 15 microns or less are most suitable for controlling odors.

Fluid, such as but not limited to, water, is preferably supplied to the misting ring 44 through the use of a hose or a tube 48 that is connected to a fluid source such as a water tank or outlet (not shown), for instance, a standpipe or hydrant. The fluid flows through the misting ring 44 and out through the nozzles 46 in the form of a fine mist 50. The mist is introduced into the high velocity air flow and discharged from the distal end of the discharge tube 42 into ambient air 60 where the water particles capture and/or combine with dust and/or odor particles and fall to the ground. Water supplied to the blower unit may be delivered first to a booster pump to boost the water pressure. Filters and straining devices may be placed in line with the water source in the event potable water is not used. In order to further control dust, odors, and other contaminates, a sealant or surfactant may be added to the water or fluid to enhance the sealant characteristics of the fluid to maintain entrapped odor or dust particles on the ground.

In order to cover a large area or an elevated area, the blower unit 10 may be angled upwards into the ambient air 60. Accordingly, the frame 14 of the blower unit may be adapted for permitting rotational and angular movement of the distal end of the discharge tube. For instance, the base 12 may include a "Y"-shaped or yoke shaped bracket 62 assembly extending from the base with bifurcated arms 64 positioned on the sides of the discharge tube 42. A pair of pins 66 may extend through the upper ends of the arms 64 and engage corresponding mounting plates 68 attached to the side of the discharge tube. In order to maintain the blower unit at a desired angle, a second set of pins 69 may extend through the arms 64 and into one of a plurality of spaced apart holes 67 on the mounting plates 68.
Figure 2:
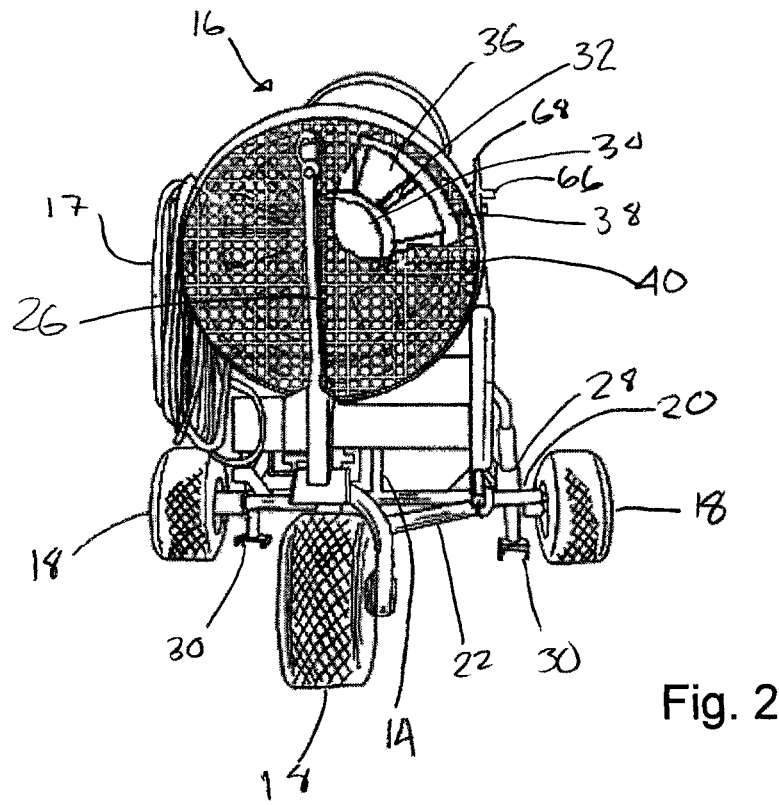
Figure 3:
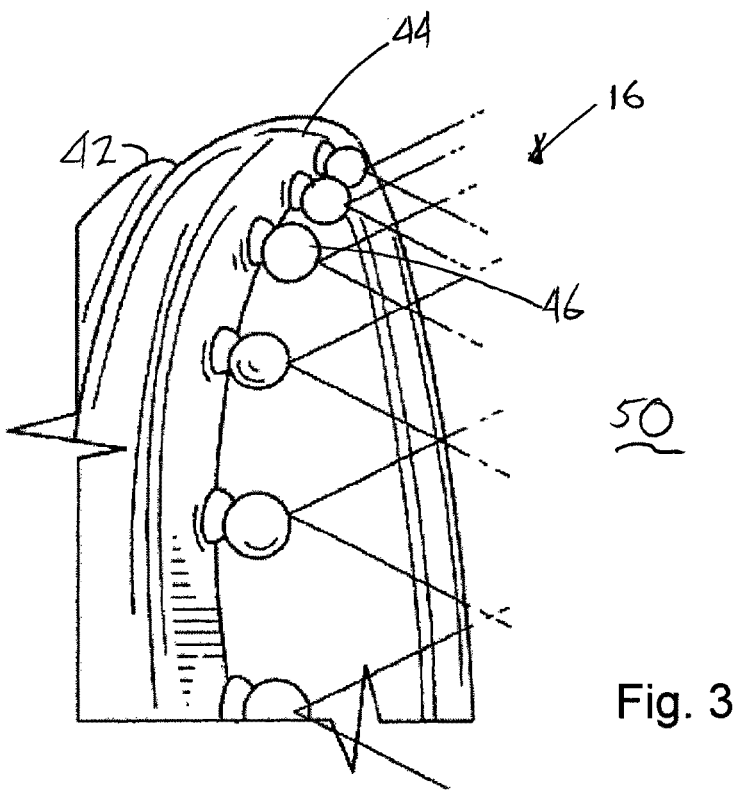
Figure 4:
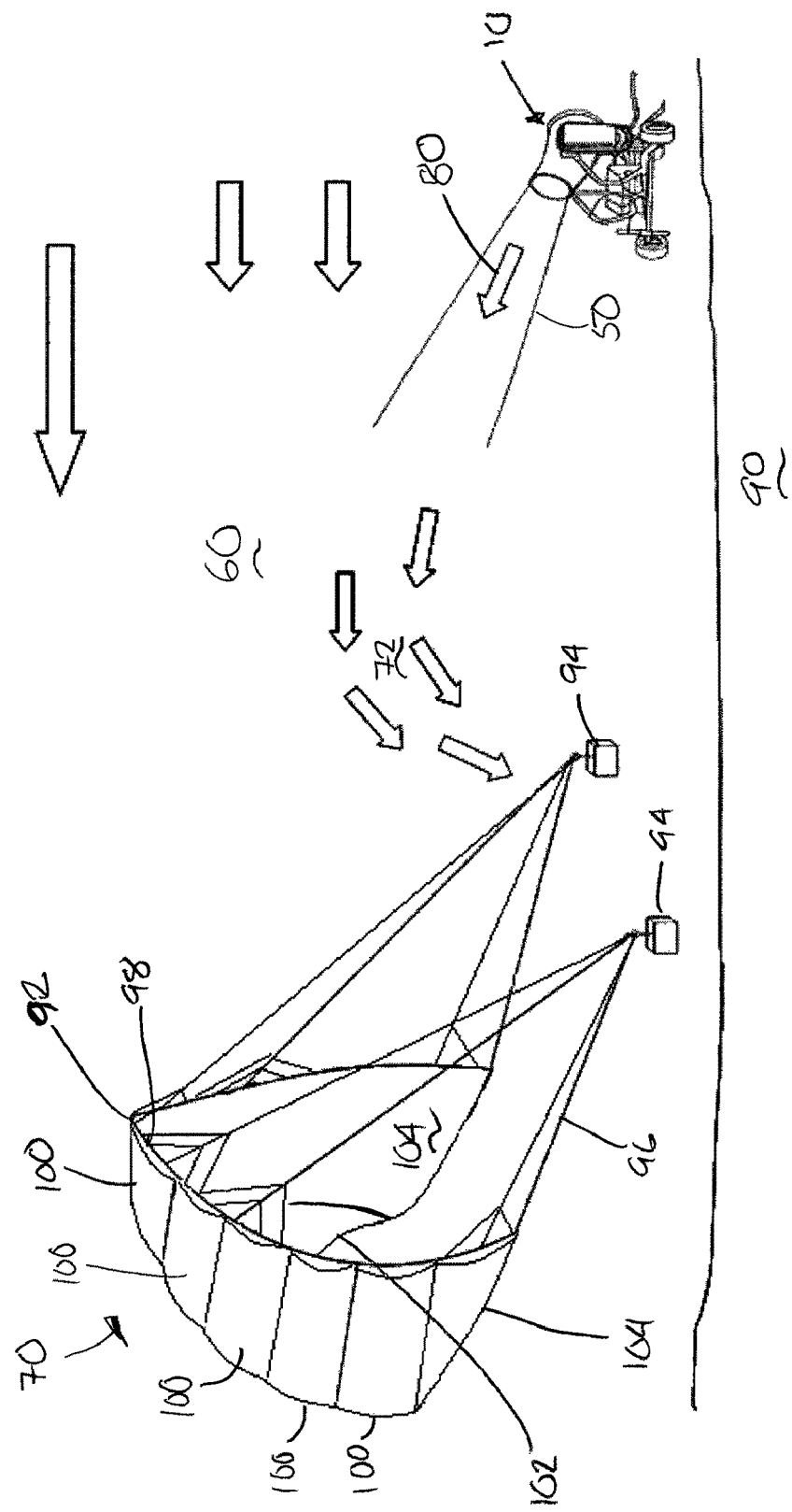
Figure 5:
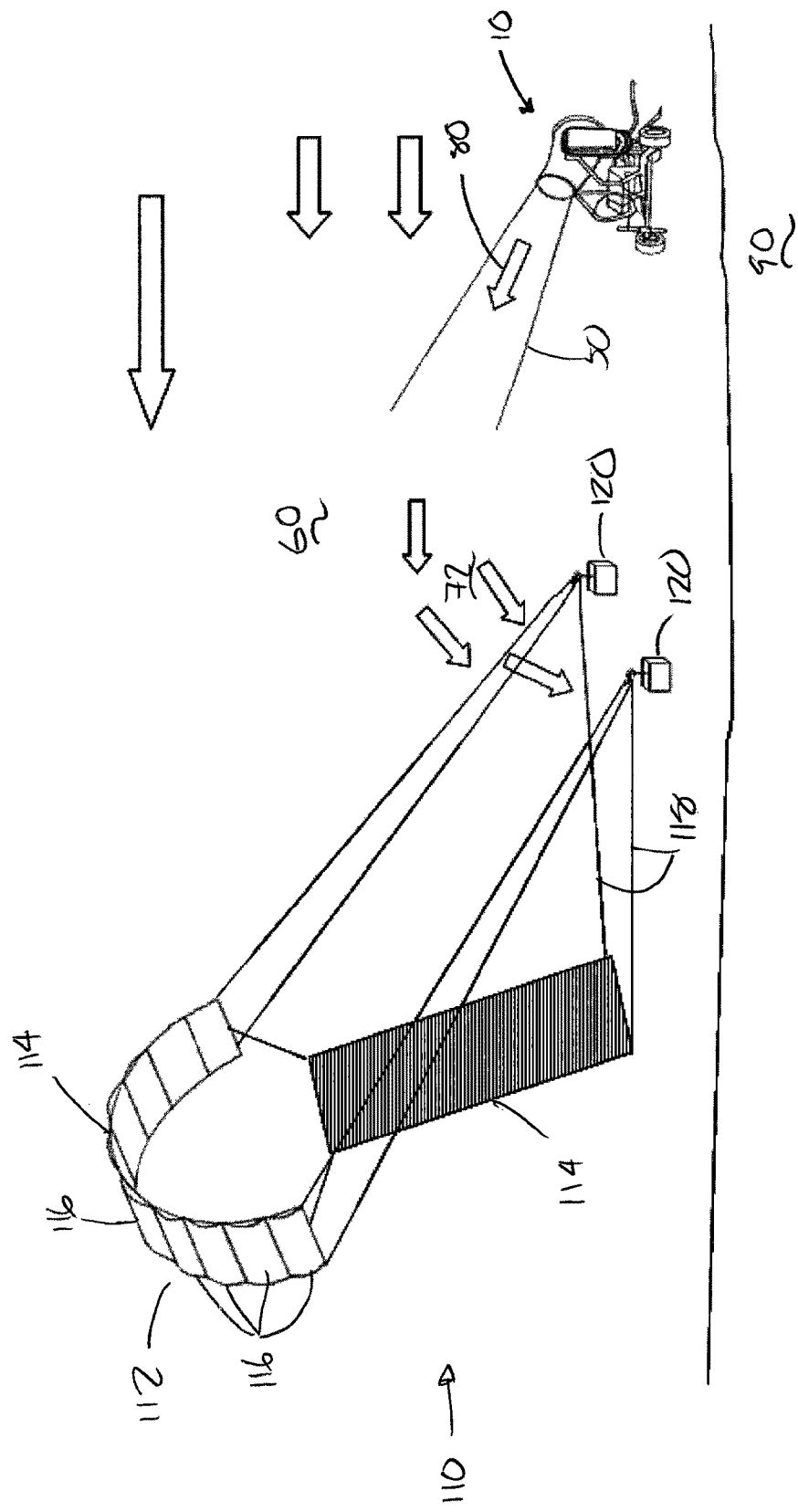

To create ambient air conditions that are further conducive to the discharged mist 50 capturing dust and/or odors, and to further enhance the sealant characteristics of the fluid to entrap and maintain the captured odor or dust particles on the ground, a baffle member 70 may be deployed downstream of the blower unit to alter a flow path 72 of the ambient air 60 flowing through the discharge path 80 of the blower unit and create ambient air conditions conducive to the fluid mist 50 capturing dust and/odors and entrapping the captured dust and/or odor particles on the ground, as discussed in greater detail below. As shown in FIGS. 4-7, a baffle member may comprise an inflatable object positioned at an elevation sufficiently above a ground level 90 downstream of the discharge path 80 of the blower unit so as to alter the flow 72 of the ambient air flowing past the discharge path of the blower unit. In one example, the baffle member may slow the flow path 72 of ambient air flowing past the discharge path of the blower member thereby allowing the fluid mist 50 discharged from the blower unit to capture odor and/or dust particles in the ambient air and the fluid sealant characteristics of the fluid to entrap the captured odor and/or dust particles on the ground. In that regard, the baffle member may also cause the ambient air flowing past the discharge path of the blower unit downward to enhance the suppression and entrapment of dust and/or odor particles on the ground. As will be described below, the baffle member may be positioned at an elevation above the ground by supports, including poles and/or tethers, or the baffle member may be rigidly connected to the ground and extend a distance sufficiently above the ground to alter the ambient air flow flowing past the discharge path of the blower unit.

FIG. 4 shows one embodiment of a baffle member 70 comprising an integral kite portion 92 deployed downstream of and at an elevation above the ground level 90 and blower unit 10. The position of the deployed baffle member 70 is secured via foundation blocks 94 and a system of ropes 96. The material forming the baffle member may comprise parachute material, such as nylon, or other semi-permeable material, for instance, sail material. To facilitate deploying the baffle member, the kite portion 92 of the baffle member may comprise a ram edge 98 leading to internal baffles 100 within the kite portion to allow the baffle member to inflate when the ram edge is positioned in a direction transverse to a direction of the ambient air flow. As shown in FIG. 4, the baffle member has a rear portion 102 integral with and extending between sides portions 104 and below the kite portion. By deploying the baffle member downstream of and at an elevation above the blower unit, the ambient air flow 60 flowing past the discharge path 80 of the blower unit is sufficiently slowed to create ambient air conditions that enhance the ability of the fluid mist 50 to capture dust and/or odors and force the captured dust and/or odor particles to return to the ground 90. The baffle member also may physically block captured dust and/or odor particles from proceeding downstream beyond the baffle member.

FIG. 5 shows an alternate embodiment of a baffle member 110. In FIG. 5, the baffle member 110 comprises a separately deployable kite portion 112 with a depending panel portion 114 that may be deployed in a direction transverse to the direction of the ambient air flow 72 flowing past the blower unit once the kite portion is elevated as desired. In FIG. 5, the kite portion of the baffle member enables the panel portion to be deployed at an elevation sufficient above the ground level 90 and blower unit 10 to alter the ambient air flow path to create the necessary ambient air conditions to enhance the mist capturing the airborne dust and/or odor particles. The kite portion 112 may be formed with an open ram edge 114 that is positioned transversely to the direction of ambient air flow so as to capture ambient air flow and inflate the kite portion by inflating internal baffles 116. The kite portion 112, and the panel portion 114 once deployed, may be securely positioned with tethers 118 extending from foundation blocks 120.

FIG. 6 shows an alternate embodiment of a baffle member 130 of FIG. 4 comprising a tube-shaped member 132. As shown in FIG. 6, the tube-shaped member 132 has an opening 134 that is aligned in a direction transverse to the direction of the ambient air flow 60 flowing past the discharge 80 of the blower unit. The opening of the tube shaped member is sized to extend at elevation above the ground level 90 and blower unit 10 sufficient to alter the ambient air flow path 72 to create the necessary ambient air conditions around the discharge path 80 of the blower unit to enhance the mist 50 capturing the airborne dust and/or odor particles. To assist in deploying the baffle member, the tube-shaped member may be provided with a ram edge leading to internal baffles so that it may be inflated similar to the kite portion of the baffle members of FIGS. 4 and 5. Alternatively, as shown in FIG. 6, the baffle member 130 may be deployed by inflating inflation passages 136 of the baffle member through an external inflation device 138, such as a blower or air pump. In FIG. 6, the opening 134 of the tube-shaped member has the inflation passages 136 extending around its periphery, and the external inflation device or blower 138 is aligned in communication with the inflation passages to directed pressurized air or gas into the inflation passages and maintain the opening in an open position. To maintain the deployed tube-shaped member 134 in position, the tube-shaped member may be anchored with tethers or ropes 140 anchored to foundation blocks 142. Louvers 144 may also extend across at least a portion of the opening of tube-shaped member to direct air flow into and through the tube-shaped member to main the tube-shaped member in an inflated and open condition. To prevent overpressurizing the interior of the tube-shaped member from transient ambient air conditions, relief flaps 146 may be provided on the skin of the tube-shaped member. The tube-shaped member 132 may also be tapered away from the opening to channel ambient air flow to a rear portion of the tube-shaped member. In FIG. 6, the inflation passages may be made from an air-impermeable material while the remaining skin portion of the tube-shaped member may comprise a semi-permeable, lightweight material such a sail, nylon or parachute material.

FIG. 7 shows an alternate embodiment of the baffle member 130 of FIG. 6 where in addition to the external inflation device 138 pressurizing the inflation passages 136 disposed around the periphery of the opening 134 of the tube-shaped member 132, the opening is maintained in the open position with supports 148, for instance, telescopic or tent-like poles.

As before, the opening of the tube shaped member 132 is sized to extend at elevation above the ground level 90 and blower unit 10 sufficient to alter the ambient air flow path 60 to create the necessary ambient air conditions around the discharge path 80 of the blower unit to enhance the mist 50 capturing the airborne dust and/or odor particles.

Figure 6:
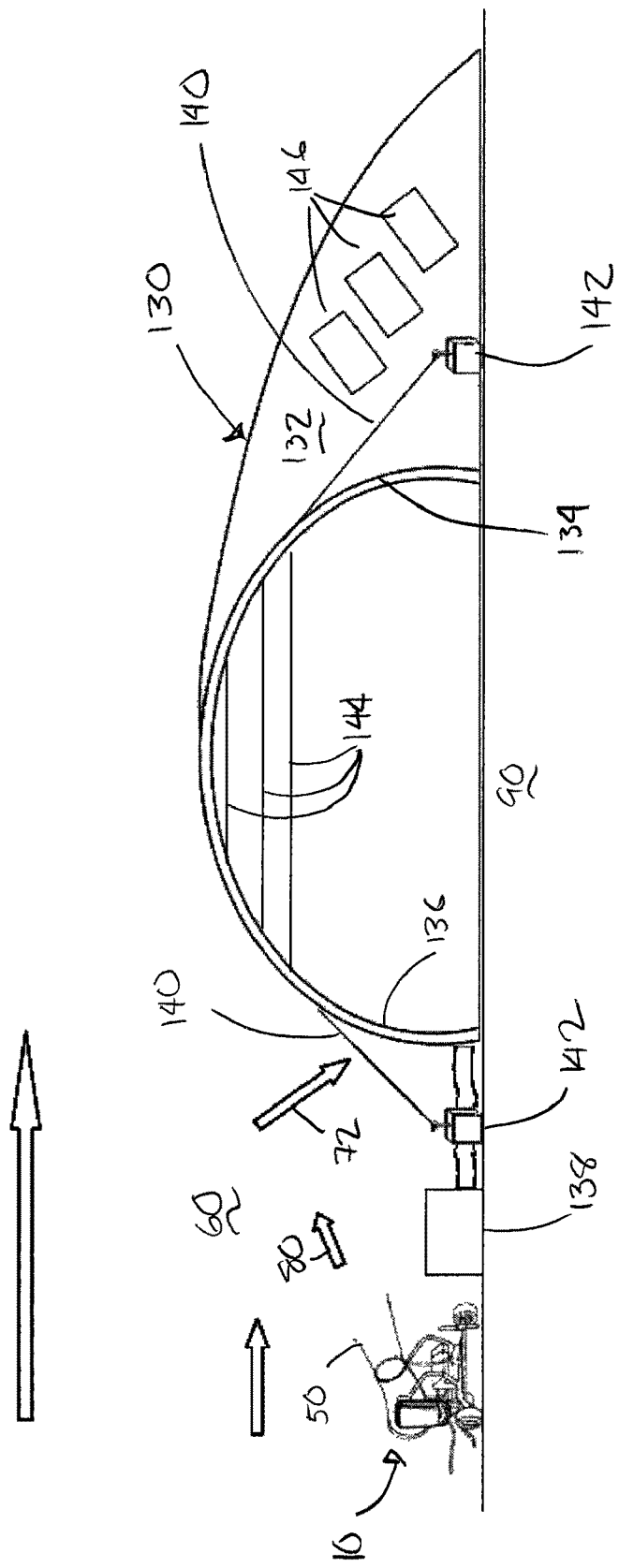
Figure 7:
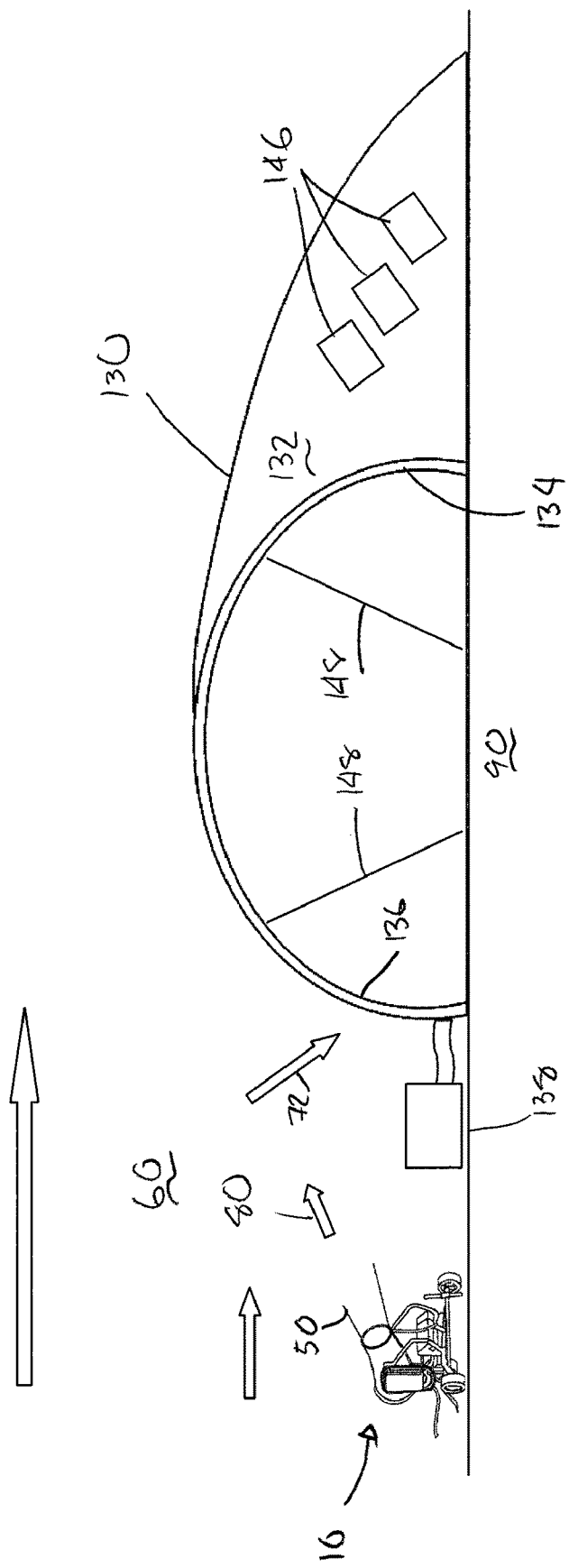
Figure 8:
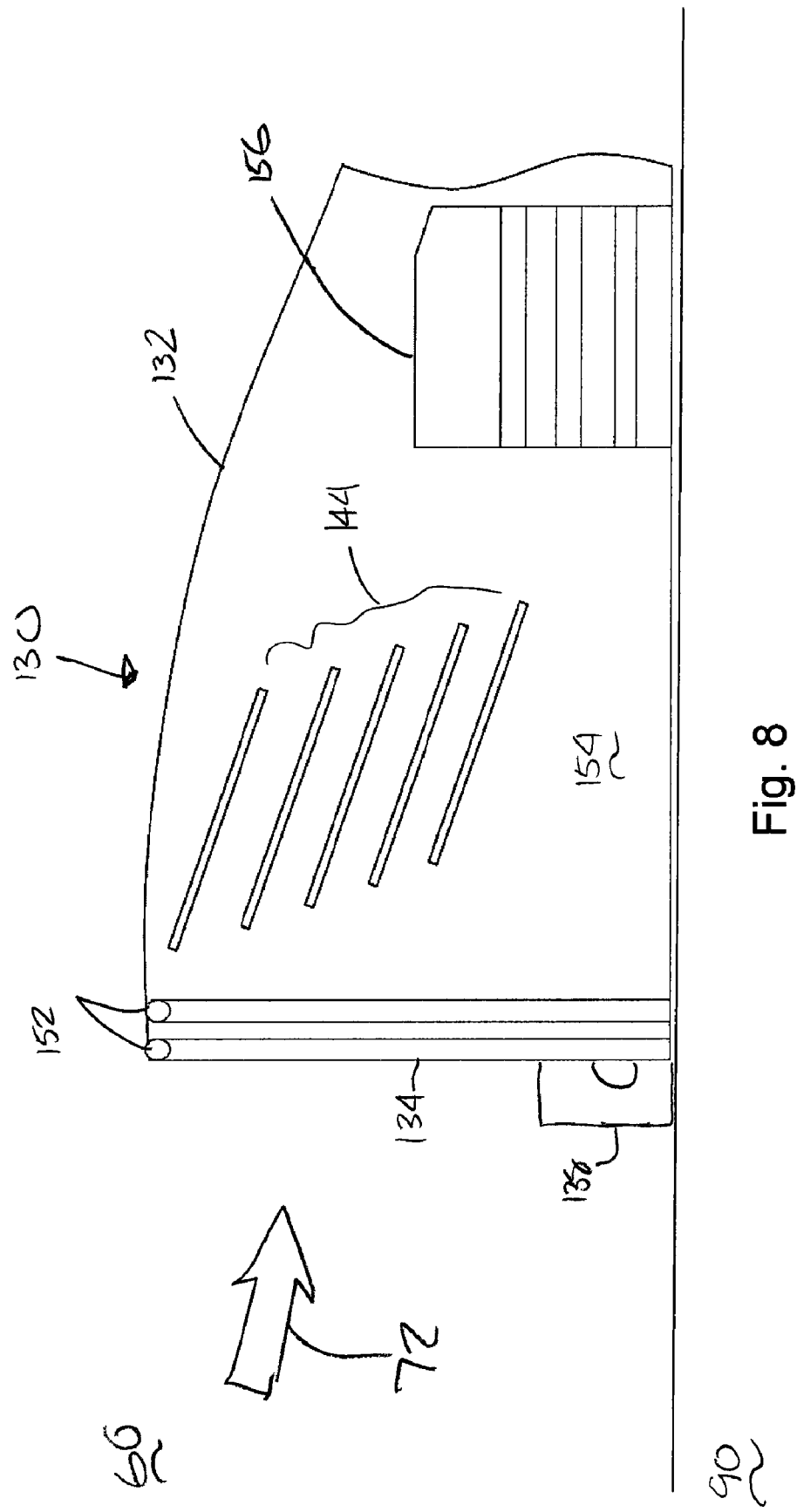

FIG. 8 shows a cross-sectional view of a baffle member 130 such as that shown in FIGS. 6 and 7. Two inflation passages 152 are provided about the periphery of the opening 134 of the tube-shaped member 132 and inflated by way of the external inflation device 138 aligned in communication with the inflation passages. The louvers 144 extend across an interior 154 of the tube-shaped member to direct a portion of the ambient air flow 60 to the rear portion of the tube-shaped member to assist in maintaining the baffle member inflated and the opening of the tube shaped member open. A filtration 156 unit is provided in the interior of the baffle unit to collect dust and/or odor particles not entrapped on the ground 90, but otherwise carried into the interior of the tube-shaped member by the ambient air flow.

It will be understood that modifications and variations may be effective without departing from the scope of the novel concepts disclosed herein, but it is understood that this application is limited only by the scope of the appended claims.

What is claimed is:

1. A method comprising:
providing a ducted fan blower unit comprising a base, a frame extending upward from the base, and a fan propelled mister attached to the frame, the fan propelled mister comprising a discharge tube and a fan disposed in the discharge tube adapted for drawing air into the discharge tube and creating a high velocity airflow exiting from the discharge tube, the discharge tube having a plurality of nozzles at its a distal end;
placing a fluid source in communication with the nozzles such that the nozzles discharge fluid particles from the discharge tube distal end;
operating the ducted fan blower unit to discharge from the discharge tube distal end the fluid particles entrained in the high velocity airflow; and
deploying a baffle member downstream of the blower unit at an elevation above the blower unit so as to alter a flow path of ambient air flowing through a discharge path of the blower unit and creating an ambient air condition conducive to the fluid particles capturing at least one of dust and odors and positioning the baffle member to slow the ambient air flow, the altered flow path of ambient air being located between the distal end of the discharge tube and the baffle member.

2. The method of claim 1 wherein the step of deploying the baffle member comprises inflating the baffle member.

3. The method of claim 2, wherein the baffle member has inflatable passages inflatable from an externally powered inflation source.

4. The method of claim 2, wherein the baffle member has inflatable passages inflatable from the ambient air flow.

5. The method of claim 1, wherein the plurality of nozzles comprises a first plurality of nozzles for creating small fluid particles of a first size and a second plurality of nozzles for creating small fluid particles of a second size.

6. The method of claim 1, further comprising positioning the baffle member to direct ambient airflow downward.

7. The method of claim 1, wherein the baffle member comprises a tube shaped member; and the step of deploying the baffle member further comprises aligning an opening of the tube shaped member in a direction transverse to a direction of the ambient air flow.

8. The method of claim 7, wherein the baffle member is tapered away from the opening.

9. The method of claim 7, further comprising deploying filtering elements in an interior of the tube shaped member.

10. The method of claim 7, further comprising deploying louvering elements in an interior of the tube shaped member.

11. The method of claim 7, further comprising deploying supports in the tube shaped member interior to maintain the tube member opening open.

12. A combination comprising:
a ducted fan blower unit comprising a base, a frame extending upward from the base, and a fan propelled mister attached to the frame, the fan propelled mister comprising a discharge tube and a fan disposed in the discharge tube adapted for drawing air into the discharge tube and creating a high velocity airflow exiting from the discharge tube, the discharge tube having a plurality of nozzles at its a distal end, the nozzles adapted to discharge fluid particles when the nozzles are placed in communication with a fluid source; and
a baffle member comprising a tube shaped member with an opening, the baffle member adapted to be deployed downstream of the blower unit at an elevation above the blower unit with ambient air located between the distal end of the discharge tube and the baffle member, the baffle member having sufficient size and air permeability so as to alter ambient airflow flowing past a discharge path of the blower unit and create an ambient air condition conducive to the fluid particles capturing at least one of dust and odors, and filter elements disposed in an interior of the tube shaped member.

13. The combination of claim 12, wherein the baffle member comprises inflatable passages.

14. The combination of claim 13, further comprising an externally powered inflation source for inflating the inflatable passages.

15. The combination of claim 13, wherein the inflatable passages are arranged on the baffle member so as to be inflatable from the ambient air flow.

16. The combination of claim 12, wherein the plurality of nozzles comprises a first plurality of nozzles for creating small fluid particles of a first size and a second plurality of nozzles for creating small fluid particles of a second size.

17. The combination of claim 12, wherein the baffle member is tapered away from the opening.

18. The combination of claim 12, further comprising louvering elements disposed in an interior of the tube shaped member.

19. The combination of claim 12, further comprising supports disposed in the tube interior to maintain the tube member opening open.

20. A method comprising:
providing a ducted fan blower unit comprising a base, a frame extending upward from the base, and a fan propelled mister attached to the frame, the fan propelled mister comprising a discharge tube and a fan disposed in the discharge tube adapted for drawing air into the discharge tube and creating a high velocity airflow exiting from the discharge tube, the discharge tube having a plurality of nozzles at its a distal end;
placing a fluid source in communication with the nozzles such that the nozzles discharge fluid particles from the discharge tube distal end;
operating the ducted fan blower unit to discharge from the discharge tube distal end the fluid particles entrained in the high velocity airflow;

inflating a baffle member; and deploying the baffle member downstream of the blower unit at an elevation above the blower unit so as to alter a flow path of ambient air flowing through a discharge path of the blower unit and creating an ambient air condition conducive to the fluid particles capturing at least one of dust and odors and positioning the baffle member to slow the ambient air flow.

21. A combination comprising:

a ducted fan blower unit comprising a base, a frame extending upward from the base, and a fan propelled mister attached to the frame, the fan propelled mister comprising a discharge tube and a fan disposed in the discharge tube adapted for drawing air into the discharge tube and creating a high velocity airflow exiting from the discharge tube, the discharge tube having a plurality of nozzles at its a distal end, the nozzles adapted to discharge fluid particles when the nozzles are placed in communication with a fluid source; and a baffle member comprising a tube shaped member with an opening and inflatable passages, the baffle member adapted to be deployed downstream of the blower unit at an elevation above the blower unit, the baffle member having sufficient size and air permeability so as to alter ambient airflow flowing past a discharge path of the blower unit and create an ambient air condition conducive to the fluid particles capturing at least one of dust and odors, and filter elements disposed in an interior of the tube shaped member.

* * * * *